(12) United States Patent
Krill et al.

(10) Patent No.: US 6,605,746 B2
(45) Date of Patent: Aug. 12, 2003

(54) PROCESS FOR THE PREPARATION OF 6-METHYLHEPTANONE

(75) Inventors: Steffen Krill, Hanau (DE); Stephan Kretz, Biebergemünd (DE); Achim Schneider, Alzenau (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 10/096,959

(22) Filed: Mar. 14, 2002

(65) Prior Publication Data

US 2003/0040645 A1 Feb. 27, 2003

(30) Foreign Application Priority Data

Mar. 14, 2001 (DE) .......................................... 101 12 099

(51) Int. Cl.$^7$ .............................................. C07C 45/72
(52) U.S. Cl. ...................................... 568/390; 568/392
(58) Field of Search .................................. 568/390, 392

(56) References Cited

U.S. PATENT DOCUMENTS

| | | |
|---|---|---|
| 3,316,303 A | 4/1967 | Mertzweiller et al. |
| 3,574,773 A | 4/1971 | Mueller et al. |
| 3,983,175 A | 9/1976 | Tamai et al. |
| 3,984,475 A | 10/1976 | Tamai et al. |
| 4,005,147 A | 1/1977 | Fischer et al. |
| 4,146,581 A | 3/1979 | Nissen et al. |
| 4,212,825 A | 7/1980 | Nissen et al. |
| 5,955,636 A | 9/1999 | Kido et al. |

FOREIGN PATENT DOCUMENTS

| | | |
|---|---|---|
| DE | 1259876 | 2/1968 |
| DE | 1268135 | 5/1968 |
| DE | 2625541 A1 | 12/1977 |
| GB | 1246695 | 1/1969 |
| WO | 9631454 A1 | 10/1996 |
| WO | WO 02/20449 | 3/2002 |

Primary Examiner—Johann Richter
Assistant Examiner—Sikarl A. Witherspoon
(74) Attorney, Agent, or Firm—Venable LLP; Ann S. Hobbs (57) ABSTRACT

A process for the preparation of methylheptanone and corresponding homologous methyl ketones involves the cross-aldolization of acetone with the corresponding aldehyde. The polar catalyst phase is introduced with acetone and an organic auxiliary solvent phase to form a two phase mixture in the presence of hydrogen. The corresponding aldehyde is then added at temperatures between 40° C. and 200° C. The process can be run in a continuous manner with the polar catalyst phase being recyled after regeneration. The use of the non-polar auxiliary solvent(s) increase yield and selectivity.

17 Claims, 1 Drawing Sheet

Figure 1

PROCESS FOR THE PREPARATION OF 6-METHYLHEPTANONE

The invention relates to an improved process for the preparation of 6-methylheptan-2-one and corresponding homologous methyl ketones, in particular phytone and tetrahydrogeranyl acetone, by aldolization of aldehydes with acetone in the presence of a polyhydric alcohol or aqueous solutions and suspensions, respectively, of an aldolization catalyst and a heterogeneous hydrogenation catalyst and a non-polar additive or auxiliary solvent.

The invention relates in particular to an industrial process for the production of methyl ketones by condensation of the corresponding aldehydes with acetone under hydrogenating conditions, wherein the methyl isobutyl ketone which is formed by acetone dimerization as a by-product is used as a selectivity-increasing additive and is partially circulated.

Methyl ketones, in particular 6-methylheptan-2-one, tetrahydrogeranyl acetone and phytone, are important intermediates and starting materials for the manufacture of fragrances, pharmaceutical products and animal feed additives (J. Org. Chem., 32 (1967), 177; J. Org. Chem., 28 (1963), 45; Bull. Soc. Chim. Fr. (1955), 1586), in particular of isophytol, which in turn constitutes a central building-block of vitamin E synthesis.

The preparation of methyl ketones, in particular methylheptanone, is described in the relevant literature, with various synthesis strategies being adopted. For instance, isoamyl halides and acetoacetic esters can be coupled with one another in a nucleophilic substitution reaction in the presence of stoichiometric quantities of a base(route A), with the β-ketoester which arises as an intermediate being decarboxylated, with dissociation of the corresponding alcohol and carbon dioxide. Poor atom efficiency, the high level of waste $CO_2$, alcohol production, and the salt burden which arises (Wagner et al., "Synthetic Organic Chemistry", 327, John Wiley & Sons, Inc.) make the process uneconomic.

Another synthesis strategy proceeds initially from the preparation of various unsaturated methylheptanone derivatives such as, for instance, 6-methyl-5-hepten-2-one or 6-methyl-3,5-heptadien-2-one (route B), which in a separate reaction step are hydrogenated to methylheptanone in the presence of heterogeneous catalysts (Izv. Akad. Nauk SSSR, Ser. Khim. 5 (1972), 1052). Disadvantages of this method are the cost of preparing the methylheptanone and the need for the method to be carried out as a multi-stage process.

A further possibility is oxidation of 6-methyl-5-hepten-2-ol (route C), as described in Recl. Trav. Chim. Pays Bas, 28, 116 (1909), or treatment of the alkenol with phosphoric acid and phosphorus(V) oxide (route D) in accordance with Bull. Soc. Chim. Fr., 1799, (1963). Both of these methods are unsuitable for the industrial preparation of methylheptanone because stoichiometric quantities of the corresponding reagents are consumed and synthesis of the educt is multi-stage and complex.

Numerous synthesis strategies have focused on the accessibility of 6-methyl-5-hepten-2-one from which, as outlined above (route B), the corresponding methylheptanone can be prepared efficiently by catalytic hydrogenation. Manufacturers of fragrances, aromas and vitamins have been fairly quick to recognize that 6-methyl-5-hepten-2-one constitutes a central intermediate from which it is possible to produce diverse vitamins, inter alia vitamin E and vitamin A, carotinoids and fragrances. The most important processes are discussed here by way of example.

Industrial use is made of a multi-stage process proceeding from acetone (route E) which in the first stage is converted in ammonia to methylbutinol in the presence of basic catalysts. Following Lindlar hydrogenation to methylbutenol a reaction with diketene then takes place and the intermediate which forms "in situ" is converted to methylheptenone in a Caroll rearrangement (J. Org. Chem., 23, 153, (1958). It is obvious that the large number of stages in the process and the use of diketene and acetylene, and the associated high level of safety technology required, severely restrict the industrial applicability of the process.

A further process for the preparation of methylheptenone includes the pressure reaction of isobutene with formaldehyde and acetone (route F). The process conditions, which necessitate the application of high temperatures and pressures in order to obtain good conversions and selectivities, are, however, associated with high capital costs and restrict the applicability of the process (DE 12 59 876; DE 12 68 135; U.S. Pat. No. 3,574,773).

A different route to methylheptenone, which achieves its aim under moderate conditions, is a two-stage process which has in the meantime been scaled up to the industrial level. In the first step isoprene is reacted with HCl gas in the presence of a Cu-I halide, with an isomer mixture of the corresponding allyl chlorides arising. In a two-phase reaction with aqueous sodium hydroxide solution the terminal prenyl chloride is coupled with acetone in the presence of a phase transfer catalyst (route G). This process suffers from the disadvantages that a stoichiometric quantity of salt arises, and only moderate yields, of the order of 70%, are achieved (U.S. Pat. Nos. 3,983,175 and 3,984,475).

-continued

Weg F:

Weg G:

In view of the problems indicated, selection of any of the synthesis strategies which have been indicated would appear to be uneconomic for the preparation of methylheptanone. In particular the route to 6-methylheptan-2-one by way of 6-methyl-5-hepten-2-one according to the prior art is associated only with a large number of stages and considerable capital cost.

A route to a double bond isomer of 6-methyl-5-hepten-2-one, namely 6-methyl-3-hepten-2-one, by cross-aldol condensation of isovaleraldehyde and acetone, in the presence of an aqueous alkali compound as a catalyst (Nippon Kagaku Kaishi, 59, 224 [1938]) constitutes an alternative process. The moderate reaction temperature which is adjusted in order to obtain high selectivities is also responsible for the reaction stopping at the β-hydroxyketone stage (Bull. Soc. Chim. Fr., 112, [1957]).

In GB 1,246,698 acetone and isovaleraldehyde are reacted together at temperatures of >200° C. and pressures of >30 bar, with only modest conversions of approx. 25% being obtained and acetone being used in a molar excess of 4 equivalents. In addition to the use of aqueous sodium hydroxide as a reaction catalyst, heterogeneous oxides are also described as aldolization catalysts.

DE-OS 26 15 308 (q.v. also U.S. Pat. No. 4,146,581) describes the use of catalytic quantities of rare earth oxides and simultaneously a heterogeneous hydrogenation catalyst (one or more metals from Group VIII of the Periodic Table) for the cross-aldolization of symmetrical ketones with low aldehydes (q.v. the reaction of acetone with isovaleraldehyde, Example 12), with the reaction being carried out at higher temperatures under hydrogenating conditions (in the presence of hydrogen, preferably at between 20 and 30 bar). According to a variant on this process, the aldolization catalyst utilized is not an oxide but a corresponding lipophilic salt (for example stearate). A disadvantage of this essentially sound process is the fact that in order to obtain high selectivities the ketone is used in a clear excess (3 to 5 equivalents in relation to the aldehyde utilized) and aldehyde conversion is incomplete. In this method a not inconsiderable component of the unreacted methylheptenone is also obtained in addition to the desired methylheptanone. No detail is provided as to the service lives of the heterogeneous systems which are used.

DE-OS 26 25 541 (corresponds to U.S. Pat. No. 4,212, 825) also focuses on a method for the direct preparation of higher saturated ketones, in particular 6-methylheptanone, by cross-aldolization of acetone with 3-methylbutanal by the use of a heterogeneous supported contact catalyst which contains zinc oxide as the aldolizing component and nickel, cobalt or copper as the hydrogenating component. Disadvantages of this method are incomplete conversion, an unsatisfactory hydrogenation yield and the by-products which arise as a result of consecutive reaction of methylheptanone with a further equivalent of isovaleraldehyde (the product mixture contains 2,10-dimethylundecan-6-one and unsaturated precursors). Catalyst preparation is moreover costly. No detail is provided as to the long-term activity of the catalyst.

The use of zinc oxide "per se" as an aldolization catalyst for the preparation of the corresponding α, β-unsaturated ketones is described in U.S. Pat. No. 4,005,147. The use of lipophilic zinc salts in the presence of a hydrogenation catalyst is described in U.S. Pat. No. 3,316,303, in which considerable quantities of the unwanted alcohol result in particular from the use of an unsuitable hydrogenation catalyst (sulfide of the elements Mo, Ni, W or of a cobalt carbonylation catalyst).

A further approach to the preparation of 6-methylheptanone is described in WO 96/31454 according to which, in a two-stage process, in a first stage the cross-aldolization of acetone with isovaleraldehyde is first carried out in the presence of aqueous sodium hydroxide solution and, after a mixture containing 4-hydroxy-6-methyl-heptan-2-one has been obtained, dehydration and hydrogenation take place in the presence of a catalytic quantity of Brönstedt acid and a heterogeneous noble metal hydrogenation catalyst. It is obvious that a multi-stage process, in particular the need to switch the catalyst medium from basic to acid, does not constitute a satisfactory solution to the present problems. In order to achieve high yields, moreover, an acetone excess of between 3 and 5 equivalents in relation to isovaleraldehyde is adjusted.

Another process is described in U.S. Pat. No. 5,955,636, in which aldolization of isovaleraldehyde with acetone is carried out in the presence of an aqueous sodium hydroxide solution and a heterogeneous noble metal hydrogenation catalyst, with the hydrogenation catalyst being suspended in an initial charge of acetone, and simultaneously both the aqueous sodium hydroxide solution and also isovaleraldehyde being dispensed into this suspension at elevated temperatures.

A disadvantage of this process is the cost of the process engineering which must be deployed for the simultaneous dispensing of the two solutions. After the reaction the heterogeneous hydrogenation catalyst must be removed by filtration, and this is then followed by phase separation, with the upper phase containing the substance of value, 6-methylheptanone, and the lower phase the aqueous sodium hydroxide solution diluted by the water of reaction. The conversions achievable by this process are approx. 97 to 98%, the yields in relation to isovaleraldehyde are approx. 87%. It becomes apparent when reproducing the patent that a substantial proportion of the isovaleraldehyde is hydrogenated to undesirable 3-methylbutan-1-ol. No detail is provided as to recycling and/or reactivation of the aqueous catalyst phase which contains both the alkaline aldolization catalyst and also the heterogeneous hydrogenation catalyst.

In the processes cited as prior art complete conversion is not normally sought because the selectivity of the aldolization falls as the conversion increases, a phenomenon attributed to consecutive reactions between the methylheptanone which has been formed and further equivalents of isovaleraldehyde, or to reactions of one of the intermediates β-hydroxyketone or methylheptenone.

A further considerable disadvantage of the processes described is the need to utilize a large acetone excess in order to obtain high isovaleraldehyde selectivities. However, acetone tends under the given conditions to dimerize to mesityl oxide, which under hydrogenating conditions converts to methyl isobutyl ketone. In the processes described as prior art this homoaldolization of acetone constitutes a considerable side-reaction which markedly reduces the acetone selectivity and is manifested in a high specific consumption of ketone.

In particular all the proposed processes neglect the issue of how to recycle the catalyst phase, in particular the hydrogenation catalyst which dictates the economics of the process.

No economic process has hitherto been known which describes the preparation of methyl ketones, in particular 6-methylheptan-2-one, in which satisfactory yields are obtained at complete conversions (conversions >99%). Furthermore, a satisfactory process for preventing the undesirable by-product formation which results from the hydrogenation of isovaleral to 3-methylbutanol, and thus for reducing the specific consumption of isovaleral, has hitherto proved elusive.

The object of this invention was to find a process for the generation of methyl ketones by cross-aldolization of acetone with the corresponding aldehydes under hydrogenating conditions, which a.) enables the corresponding methyl ketones to be prepared at optimal yields and purities with complete conversion (>99%) of the aldehyde utilized, while avoiding a costly process regime, namely the simultaneous addition of both the aqueous alkali solution and the aldehyde, b.) enables a simple recycling of the unreacted or unconsumed educts and auxiliary solvent, in particular acetone, the active hydrogenation catalyst, and thus allows consistently stable yields and process conditions to be achieved with repeated utilization of the reactivated catalyst, and c.) prevents undesirable hydrogenation of the aldehyde utilized to the corresponding primary alcohol.

The process according to the invention is an industrial circulating process with partial recirculation of the auxiliary solvent and/or methylheptanone, in which the non-polar auxiliary solvents according to the invention exert a selectivity-enhancing effect. A further aspect of the present invention is the utilization of the said methyl ketones as an educt for the preparation of isophytol and vitamin E acetate as a result of passing successively through reaction sequences $C_2$, $C_3$ chain lengthening and partial hydrogenation steps.

The invention relates to a process for the preparation of methyl ketones corresponding to the general formula (1)

wherein x represents a number between 1 and 3 (for x=1→6-methylheptan-2-one; for x=2→tetrahydrogeranyl acetone; for x=3→phytone) by reacting hydrogen, acetone and an aldehyde corresponding to the general formula (2)

wherein x represents a number between 0 and 2 and the broken lines in each case represent olefinic double bonds, characterized in that the reaction of the components is carried out in the presence of a catalyst suspension which contains a suspended heterogeneous hydrogenation catalyst and a dissolved aldolization catalyst containing alkali metal or alkaline earth metal, and that the reaction of the components is carried out in two-phase manner, wherein the lower, water or alcohol, phase constitutes the suspension medium of the heterogenous hydrogenation catalyst and the solvent of the aldolization catalyst, and the upper phase constitutes a solution of acetone (reagent) in a non-polar auxiliary solvent, in particular methyl isobutyl ketone.

It is important that the process according to the invention is utilized as a two-phase process for the preparation of methyl ketones, in particular 6-methylheptan-2-one, by co-aldolization of aldehydes, in particular isovaleraldehyde, with acetone under hydrogenating conditions.

It has been found after intensive investigation that the problems indicated above are resolved in surprising manner, in that 1) the catalyst phase is introduced into an autoclave as an initial charge together with acetone as a two-phase mixture under hydrogen and, with efficient stirring ensured, the corresponding aldehyde is pumped in at temperatures of between 40° C. and 200° C., and after termination of the reaction, following separation of the heterogeneous hydrogenation catalyst, the upper phase which contains the substance of value (the corresponding methyl ketone along with unreacted acetone) is removed from the water phase or alcohol phase and acetone is recovered by distillation and the corresponding methyl ketone is isolated; and 2) after termination of the reaction, the methyl isobutyl ketone formed during the reaction is obtained, along with acetone, by distillation of the organic product phase, and is returned wholly or partially into the reaction as a recycle stream, wherein methyl isobutyl ketone, being a comparatively non-polar solvent, ensures that the reaction batch is two-phase at the beginning of the reaction, and optionally 3) a further non-polar auxiliary solvent is circulated when the process is carried out as a continuous process.

In particular an improved process is described for the preparation of asymmetrically substituted ketones carrying an α-methyl group, which are designated herein-below as methyl ketones, by reacting the corresponding aldehydes with acetone under hydrogenating, dehydrating and aldolizing conditions, wherein the educts used and the products arising have low solubility in the catalyst phase which contains both the hydrogenation catalyst and also the alkaline dehydration and aldolization catalyst.

The addition according to the invention of a non-polar auxiliary solvent, in particular the recycling of this auxiliary solvent when the process is operated as a continuous process, enables previously undescribed yields of up to 98% in relation to aldehyde utilized, to be achieved.

A further aspect of the invention is the two-phase reaction regime with use of a polyhydric polar alcohol as the suspending medium of the heterogeneous hydrogenation catalyst or aqueous solutions of the said polyhydric alcohols or in the simplest instance, water itself, and the separation of the product phase from the active catalyst phase following filtration of the hydrogenation catalyst, phase separation and working-up of the two phases, with recirculation of unreacted educts and auxiliary substances.

Admittedly, methyl isobutyl ketone is formed as a by-product of the undesirable acetone homoaldolization in all the processes described in the prior art, yet in these processes the methyl isobutyl ketone concentration increases only as the duration of the reaction increases, that is to say, at the beginning of the reaction absolutely no methyl isobutyl ketone is present.

According to the present process, by recycling methyl isobutyl ketone and/or methylheptanone from the working-up of the products, a concentration of methyl isobutyl ketone and/or methylheptanone sufficient to increase markedly the yield of the reaction is now adjusted even at the beginning of the reaction.

After the two-phase reaction mixture has been introduced as the initial charge, the optionally unsaturated aldehyde is dispensed-in, such that the "in situ" concentration thereof in the reaction mixture is at all times below 20 mol. % in relation to acetone. After the reaction has run, the two-phase mixture in which the hydrogenation catalyst is suspended is filtered, with the heterogeneous hydrogenation catalyst being separated and an unequivocally two-phase mixture resulting. The phase containing the aldolization catalyst is separated. The working-up of the two phases by distillation recovers unreacted acetone virtually quantitatively along with smaller aldehyde residues and enables the methyl ketones which are desired as the product to be isolated at purities of >99%.

Taking as an example the acetonization of 3-methylbutyraldehyde (isovaleraldehyde) with preparation of methylheptanone, the reaction is outlined in the diagram below. The compounds shown in brackets are passed through as intermediates:

Catalyst phase here means a phase which contains the aldolization catalyst and the hydrogenation catalyst. The catalyst phase is itself likewise two-phase because the aldolization catalyst is present dissolved and the heterogeneous hydrogenation catalyst is suspended.

The process according to the invention substantially improves the process regime over that of the method described in the prior art, in that the dispensing of only one component is necessary in order for high selectivities to be achieved, and virtually quantitative yields of the desired methyl ketones in relation to aldehyde utilized can be achieved. The circulating of a non-polar auxiliary solvent, in particular the recycling of methyl isobutyl ketone or of methylheptanone itself, the product of the reaction, represents only a minor expense because methyl isobutyl ketone necessarily arises in the process as a by-product of acetone dimerization and must be separated from the product by distillation.

The high yields achieved result in a dramatic reduction in high-boiling by-products which promote the deactivation of the hydrogenation catalyst and severely limit its recyclability. Avoiding the formation of 3-methylbutanol by isovaleral hydrogenation, which arises when working in accordance with U.S. Pat. No. 5,955,636, facilitates product isolation by obviating the need to carry out corresponding separating operations.

In the highly selective process according to the invention (sic) the recyclability of the heterogeneous hydrogenation catalyst is unrestricted. Under optimal conditions the catalyst may be utilized up to 30 times or more with no appreciable loss of hydrogenating activity.

The hydrogenation catalyst is separated by standard industrial measures, in the simplest instance by filtration. The catalyst phase and product phase are in the simplest instance separated by simple decanting. The catalyst phase thus obtained contains more or less all the water of reaction which arises as a result of the condensation, thus, by avoiding formation of azeotropes between water and the carbonyl compounds or other substances present, substantially facilitating the working-up by distillation of the organic product phase. The catalyst phase contains the unconsumed alkaline aldolization catalyst and the alkali salt or alkaline earth salt of the acid corresponding to the aldehyde, the product of a Cannizzaro reaction which is observed as a side-reaction. The sodium salt of isovaleric acid arises as a by-product of the reaction of isovaleral with aqueous sodium hydroxide solution.

Before re-use of the water phase or alcohol phase the quantity of alkali consumed by side-reactions is merely replenished.

The process according to the invention consequently makes possible an industrial one-pot concept for the preparation of methyl ketones, in which the catalyst phase may be, optionally completely, returned after the reaction has been carried out and the phases have been separated. In a different variant according to the invention the alkaline catalyst solution is discarded after removal of the organic constituents and optionally neutralization.

The reaction regime provides simple dispensing of the aldehyde into the two-phase mixture of catalyst phase, acetone and non-polar auxiliary solvent, in particular methyl isobutyl ketone, thus giving rise to only minor control engineering costs. In this way a safe process regime is further ensured because heat which is generated is simply restrained by interrupting or slowing down the dispensing of aldehyde.

The first aspect of the invention relates to a process for the preparation of methyl ketones, in particular 6-methylheptan-2-one, from the corresponding carbonyl compound and acetone, characterized in that both the alkaline condensation catalyst and also the heterogeneous hydrogenation catalyst are dissolved and suspended, respectively, in a polyhydric lipophobic alcohol and/or water, and the reaction is carried out in two-phase manner in the presence of a non-polar auxiliary solvent, in particular methyl isobutyl ketone.

This first aspect also includes the method by which the lipophobic alcohol phase or water phase containing the catalysts, acetone and the auxiliary solvent is introduced as an initial charge into an autoclave under a moderate hydrogen pressure and the aldehyde component is dispensed into the two-phase mixture of acetone/auxiliary solvent and catalyst phase. It should be ensured here that the aldehyde concentration in the reaction solution should be selected to be as low as possible and does not exceed a concentration of 20 mol. % in relation to acetone utilized. This method can be realized in simple manner if the aldehyde addition takes place over a dispensing period of from 0.5 to 5 hours, at a corresponding reaction temperature. The presence of the auxiliary solvent even at the beginning of the reaction produces two-phase conditions, such that the product arising is removed from the catalyst phase at the moment of formation, in the sense of a reactive extraction.

In order to aid understanding, the reaction will be explained by way of example at this juncture, taking as the example the reaction of acetone with isovaleraldehyde for the preparation of 6-methylheptan-2-one. The reaction proceeds "in situ" by way of the aldolization 'stage, with the corresponding β-hydroxyketone arising, which is not isolated. Under the reaction conditions dehydration to 6-methylhept-3-en-2-one takes place, and this is hydrogenated selectively to the corresponding methyl ketone by the hydrogenation catalyst which is distributed homogeneously in the lipophobic alcohol phase.

BRIEF DESCRIPTION OF DRAWINGS

The process, which exemplifies the preparation of methylheptanone proceeding from isovaleral and acetone in the presence of sodium hydroxide solution and a Pd-activated carbon contact catalyst, is illustrated in FIG. 1.

The presence of an auxiliary solvent which is utilized at a concentration of at least 1 wt. % in relation to the hydrophobic solution which contains catalysts is characterizing for the present process. According to the present invention, use of the auxiliary solvent in a quantity of from 1 wt. % to 200 wt. % in relation to the catalyst phase used has the effect of boosting the yield and selectivity of the reaction. An auxiliary solvent quantity of from 5 wt. % to 50 wt. % in relation to catalyst phase is particularly preferred. When the preferred auxiliary solvent methyl isobutyl ketone, the methyl ketone which is desired as the product, is utilized, or mixtures of these components are utilized, the corresponding quantity of auxiliary solvent is adjusted by simple recycling of the streams from the working-up part which contain these components.

The molar ratio of isovaleraldehyde to acetone is not critical to the reaction and may be varied within a broad range, however acetone is normally utilized as a component in excess in order to achieve a high product selectivity in relation to isovaleraldehyde and a high aldehyde conversion. Good results are obtained when a molar ratio of isovaleraldehyde to acetone of from 1:0.5 to 1:10, preferably 1:1 to 1:5, is utilized.

Basic compounds are generally utilized as aldolization catalysts for the cross-aldolization. Suitable basic compounds are, for example, hydroxides and carbonates of alkali compounds and alkaline earth compounds of the elements lithium, sodium, potassium, magnesium, calcium or barium, with, of these compounds, sodium hydroxide and potassium hydroxide as well as barium hydroxide and calcium hydroxide being particularly preferred on account of their ready availability. Other components may also substantially be utilized, provided that there is good solubility in the matrix of the polar catalyst phase (water or polyhydric alcohols). The catalyst phase is prepared in simple manner by dissolving the corresponding bases, optionally with heating. In accordance with a further variant according to the invention, the salts in the form of their aqueous solutions are dissolved in the water phase or alcohol phase. It is also possible to utilize mixtures of different stoichiometries of the named compounds as the aldolization catalyst.

Sugar alcohols having a carbon skeleton having 3 to 6 carbon atoms, in particular glycerol, but also other di- to hexahydric alcohols, may be used as the polyhydric alcohols within the meaning of the present invention. The following alcohols might be named at this juncture by way of example: ethylene glycol, propanediol, butanediol, glycerol, erythritol and isomeric tetritols, pentaerythritol, various pentitols such as arabitol and xylitol, hexitols, and polyhydric alcohols, such as inositol, which are not derived from sugar alcohols, as well as related compounds, isomers and homologues.

When polyhydric alcohols are used as the catalyst matrix alcoholates of low alcohols, which have good solubility in polyhydric alcohol, may also be utilized as the aldolization catalyst. The following compounds from these substance classes might be named by way of example: methanolates, ethanolates, isopropanolates, butanolates and corresponding branched compounds and homologues. However, it must be noted that the use of the corresponding alcoholates has no substantial advantages over, for instance, the favorable and readily available hydroxides. Since water arises in the reaction "in situ", the alcoholates change into the corresponding metal hydroxides, with the various alcohols arising. Amides also catalyze the reaction effectively in this sense.

The polyhydric alcohol, in particular glycerol or a different sugar alcohol, is used in a ratio by volume of alcohol:acetone of from 1:20 to 20:1 in relation to acetone utilized, with a ratio by volume of between 1:5 and 5:1 being particularly preferred. The use of even greater volumes of the catalyst phase, while possible, compromises the space-time yield of the reaction and is therefore undesirable. While resulting in no further advantages, a reduction in the volume of the catalyst phase also still results in a satisfactory outcome.

Water as a reaction matrix is likewise used in a ratio by volume of water:acetone of from 1:20 to 20:1 in relation to acetone utilized, with a ratio by volume of between 1:5 and 5:1 being particularly preferred. The use of even greater volumes of the catalyst phase, while possible, compromises the space-time yield of the reaction and is therefore undesirable. While resulting in no further advantages, a reduction in the volume of the catalyst phase also still results in a satisfactory outcome.

The concentration of the alkaline aldolization catalysts may be varied within broad ranges, with a concentration of between 0.1 and 20 mol. % of the corresponding base being used in order to achieve good space-time yields and selectivities in relation to aldehyde utilized. A concentration of between 0.5 and 10 mol. % is particularly preferred.

The concentration of the base in the polyhydric alcohol is normally adjusted between 0.01 wt. % and 20 wt. %. A preferred range which allows good yields and conversions to be achieved is a concentration of between 0.1 and 5 wt. %.

The reaction is normally carried out at temperatures of between 40° C. and 200° C., with temperatures of between 80° C. and 140° C. being preferred for achieving high product selectivities and a sufficiently high reaction rate. It is likewise possible to have the different sequential reactions proceed at different temperature levels. Thus, at the beginning of the reaction, the selective carrying-out of the cross-aldolization may take place at lower temperatures than the subsequent dehydration to α,β-unsaturated methyl ketone and the hydrogenation thereof to saturated methyl ketone.

According to the process according to the invention the reaction may be carried out batch-wise. In accordance with this method, the polyhydric alcohol phase, in particular the glycerol phase, or the water phase, which contains the binary catalyst system, is introduced into a pressure vessel as an initial charge together with acetone and the auxiliary solvent, stirring well, the desired hydrogen pressure is adjusted, and the batch is brought to reaction temperature. The corresponding aldehyde, in particular isovaleraldehyde, is then dispensed-in. It is also possible to introduce as an initial charge only the catalyst phase and feed-in the mixture of auxiliary solvent/acetone and isovaleraldehyde. For reasons of selectivity the first variant is preferable, and we attribute this to the fact that, with acetone as an initial charge, the stationary ratio of acetone to isovaleraldehyde is at all times sufficiently high for effective prevention of a homoaldol condensation of isovaleraldehyde with itself.

In accordance with a further implementation according to the invention of the process, the aqueous or alcoholic catalyst phase is first brought to reaction temperature, the total quantity of acetone is then added briskly, and the aldehyde is then dispensed-in slowly as normal. It is possible in this way to suppress the undesirable homoaldolization of acetone to methyl isobutyl ketone (arises under hydrogenating conditions).

In a further two-phase embodiment variant which, however, entails greater capital cost, the alcohol phase or water phase which contains only the suspended hydrogenation catalyst is introduced together with acetone as an initial charge under the desired hydrogen pressure at reaction temperature, and both the aldehyde and also an aqueous solution of the aldolization catalyst are dispensed-in.

In a further embodiment the process is operated in continuous manner, wherein the catalyst phase and the educts are brought into mutual contact, optionally in counter-current manner. The phases are separated following reaction in the reaction zone, wherein the alcoholic or aqueous phase is returned continuously to the reactor. Here, before it re-enters the reactor, the consumed catalyst (basic aldolization catalyst) is also replenished with make-up material and the educts are replenished with make-up material.

For the implementation according to the invention of the two-phase reaction the additional presence of a non-polar auxiliary solvent is necessary, and in order to achieve high selectivities, working is preferably in the presence of methyl isobutyl ketone or the methyl ketone which is desired as the product or a mixture of these components. Also, for improved reaction control, in particular for a better temperature regime to restrain the heat of reaction, inert solvents which increase the selectivity may be utilized under reaction conditions. Aliphatic hydrocarbons such as pentane, hexane, cyclohexane, heptane, octane, and branched homologues or aromatic hydrocarbons such as benzene, toluene, xylene, or ethers such as diethylether, dibutylether, methyl-tert.-butylether, tetrahydrofuran, dioxane, glymes, diglymes, 6-methylheptanone and corresponding derivatives, for example, may be utilized as solvents and auxiliary solvents. Higher aliphatic ketones having lower solubility in the glycerol phase or water phase than acetone itself are also suitable as solvents within the meaning of the invention.

Diethyl ketone, methyl ethyl ketone, diisopropyl ketone, dibutyl ketone and in particular methyl isobutyl ketone might be named by way of examples of these ketones, with methyl isobutyl ketone being preferably utilized as a solvent of the reaction because it constitutes a by-product of the reaction, which originates in the auto-aldolization of acetone.

Those very methyl ketones which are desired as the product, such as, for instance, methylheptanone or dimethyl undecanone (accessible from citral or citronellal) and partially unsaturated derivatives derived therefrom, as well as methyl isobutyl ketone, which may be returned as a part stream into the subsequent batch after working-up of the product phase by distillation, are also preferred auxiliary solvents of the reaction.

Figure 1:
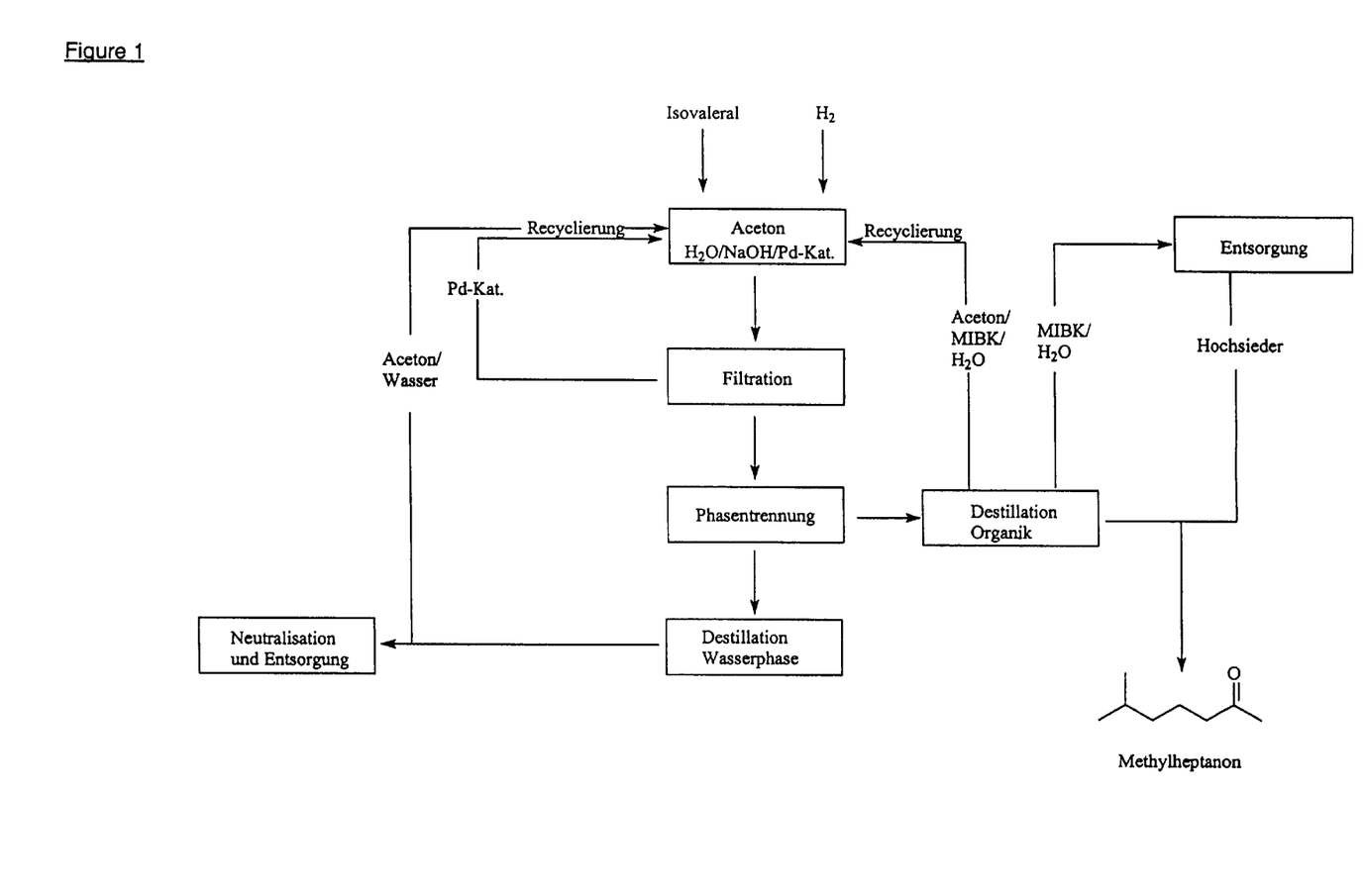

The representation, provided by way of example, of methylheptanone preparation proceeding from isovaleral and acetone makes it clear that the concentration of methyl isobutyl ketone which is necessary in the reaction in order to increase the selectivity results, after catalyst filtration and phase separation, from the recirculation of methyl isobutyl ketone and unreacted acetone (this distillate fraction also contains water).

Supported metal catalysts which have been commercially developed for the purpose and are accessible are normally used as the hydrogenation catalyst. Suitable metals which have good selectivities and service lives are in particular palladium, platinum, rhodium and nickel, which may be used in the form of the elements, oxides and mixed oxides thereof with other metals or as alloys with other metals. Suitable supports are activated carbon, aluminum oxide, silicon dioxide and further supports which are known from the literature and commercially available.

The quantity of these hydrogenation catalysts which is utilized is normally from 0.01 wt. % to 5 wt. %, with 0.1 wt. % to 3 wt. % representing a preferred catalyst quantity (the quantities of catalyst utilized are normally related to aldehyde utilized).

There are no particular restrictions in respect of the hydrogen pressure applied, with good results normally being obtained at pressures of between 1 and 40 bar. Higher pressures may also be adjusted but are undesirable in view of the engineering requirements. The range between 5 and 25 bar constitutes a preferred pressure range.

The working-up of the two-phase reaction mixture, in which in addition to product isolation and recirculation of unreacted educts the conditioning of the catalyst phase before use in a new cycle is in particular important, constitutes a further aspect of the invention.

After termination of the reaction a two-phase reaction mixture is obtained which is composed of the active catalyst phase, on the one hand, and the product phase, on the other. The water which arises in the dehydration of the β-hydroxyketone which is passed through "in situ" dissolves more or less completely in the glycerol phase or water phase and is separated more or less completely from the product by outward transfer in the catalyst phase.

After separation of the hydrogenation catalyst by filtration or other suitable measures the product phase and the catalyst phase, which form sharp phase boundaries, are separated from one another, by, in the simplest instance, removal of the supernatant product phase. The catalyst phase substantially comprises water (or a polyhydric alcohol such as glyerol or a mixture of these components), the metal salt of the carboxylate formed by Cannizzaro reaction and corresponding to the aldehyde utilized (if isovaleraldehyde and NaOH are utilized, the sodium salt of isovaleric acid) and residues of the aldolization catalyst.

The process is distinguished in that substantial quantities of by-products of the reaction are tolerated when recycling the aqueous catalyst phase, in particular of the carboxylate salts resulting from the Cannizzaro reaction, with no substantial observable effects on the selectivity and yield. After consumed aldolization base has been replenished with make-up material, the catalyst phase may be recycled or disposed of when an undesirable by-product level is reached.

The recycled catalyst phase is also characterized by its water content in addition to the carboxylate salts present. The carboxylate concentration is normally between 0.1 and 70 wt. %, the water content is adjusted between 20 and 99.9 wt. %. In order to achieve good yields and reduce the necessary rate of outward transfer, a carboxylate content of from 1 to 20 wt. % is adjusted.

When glycerol is used as the catalyst matrix the water content of the recycled glycerol phase is preferably adjusted between 1 and 50 wt. % in relation to glycerol. The sodium hydroxide solution concentration in the catalyst phase (water or polyhydric alcohol, in particular glyerol, or mixtures of these components) is within certain limits not critical to the progress of the reaction and is normally adjusted between 0.01 wt. % and 20 wt. %. A concentration of between 0.1 wt. % and 5 wt. % constitutes a preferred range.

The water concentration before recycling of the catalyst phase is, in the simplest manner, adjusted by simple concentration of the glycerol phase, with a two-phase mixture being obtained as the distillate. The organic phase comprises unreacted acetone, along with smaller quantities of methyl isobutyl ketone. The aqueous phase may be discarded, or is worked up further. The basic aldolization catalyst is replenished by addition of either the substance as such or in the form of the corresponding solutions of the bases in suitable solvents. The solvent may be either the polyhydric alcohol itself or alternatively low alcohols having 1–6 carbon atoms or also water.

The purity of the methyl ketones isolated in accordance with the process according to the invention, in particular the 6-methylheptan-2-one, which is accessible by reacting acetone with isovaleraldehyde, corresponds to a product quality such as is required for use as an educt for the synthesis of intermediates for the synthesis of vitamin E, vitamin A and various carotinoids. A product quality of >99% is normally obtained after distillation.

The present invention is explained in greater detail hereinbelow with reference to Embodiment Examples.

Comparative Example A
Two-phase Aldolization of Isovaleraldehyde and Acetone With NaOH (Without Auxiliary Solvent)

350 grams (g) water are introduced as an initial charge into a 2-liter (l) autoclave with a mechanical stirrer, and 6.5 g hydrogenation catalyst (Pd on carbon, 5 wt. %, E 101 R/W Degussa AG, $H_2O$ content 53.9%) are suspended in the water. 5 g NaOH (0.125 mole; 2.5 mol. % in relation to isovaleraldehyde) are added to this suspension. When NaOH has passed into solution, 436 g (7.5 mole) acetone are added to this suspension. A hydrogen pressure of 15 bar is adjusted at room temperature, with intensive stirring. The two-phase mixture is heated to 105° C. 431 g isovaleraldehyde (4.96 mole; from Celanese; 99% by gas chromatographic analysis (GC)) are dispensed by HPLC pump from an initial charge into this mixture by way of a submerged tube. The molar ratio of aldehyde to acetone is thus 1:1.5.

The dispensing period is 3 hours (h), the reaction temperature is maintained at between 105° C. and 110° C., with restraint of the heat which is generated. After the addition is completed, stirring continues for one further hour under hydrogen pressure, such that a constant pressure of 20 bar is present throughout the entire dispensing and post-reaction period. A total of approx. 115 l hydrogen is taken up by the batch.

After cooling to room temperature, the autoclave is opened and the two-phase mixture is extracted by suction using $H_2O$ as the purging medium. The catalyst is separated by filtration. After phase separation an organic phase of 799.8 g and 453.3 g of an aqueous phase are obtained.

The yield and the concentration of by-products are determined in the upper, product-containing, phase by means of quantitative GC with n-dodecane as the internal standard. In the organic phase 68.2 g methyl isobutyl ketone are detected, the result of acetone dimerization under hydrogenating conditions (corresponds to 1.36 mole acetone). 18.1% of the acetone originally utilized have hence been consumed in this side-reaction. In the aqueous phase 2.5 wt. % sodium salt of 3-methylbutyric acid are found.

Quantification shows that 596.5 g 6-methylheptanone (4.65 mole) were obtained, which, at an isovaleral conversion of 99.5%, corresponds to a selectivity of 94.2% and a yield of 93.75%.

EXAMPLE 1
Two-phase Aldolization of Isovaleraldehyde and Acetone With NaOH in the Presence of an $H_2O$-immiscible Methyl Isobutyl Ketone as the Auxiliary Solvent The procedure of Comparison Example A is followed, using identical batch sizes and conditions, but the initial charge mixture of hydrogenation catalyst, aqueous (sic) NaOH and acetone is additionally supplemented with methyl isobutyl ketone. 350 g water are introduced as an initial charge into a 2-liter autoclave with a mechanical stirrer, and 6.5 g hydrogenation catalyst (Pd on carbon, 5 wt. %, E 101 R/W Degussa AG, $H_2O$ content 53.9%) are suspended in the batch. 5 g NaOH (0.125 mole; 2.5 mol. % in relation to isovaleraldehyde) are added to this suspension. When NaOH has passed into solution, first 436 g (7.5 mole) acetone and then 35 g methyl isobutyl ketone (corresponds to 10 wt. % in relation to water) are added to this suspension.

A hydrogen pressure of 15 bar is adjusted at room temperature, with intensive stirring. The two-phase mixture is heated to 105° C. 431 g isovaleraldehyde (4.96 mole; from Celanese; 99% by GC analysis) are dispensed by HPLC pump from an initial charge into this mixture by way of a submerged tube. The molar ratio of aldehyde to acetone is thus 1:1.5.

The dispensing period is 3 h, the reaction temperature is maintained at between 105° C. and 110° C., with restraint of the heat which is generated. After the addition is completed, stirring is continued for one further hour under hydrogen pressure, such that a constant pressure of 20 bar is present for the entire dispensing and post-reaction period. A total of approx. 115 l hydrogen is taken up by the batch.

After cooling to room temperature, the autoclave is opened and the two-phase mixture is separated. The catalyst is separated by filtration and is washed first with 50 ml acetone and then with water.

After phase separation an organic phase of 807 g and 688 g of an aqueous phase are obtained. Analysis reveals that the aqueous phase still contains 2.55 g NaOH (63 mmole), that is to say approximately half of the NaOH utilized was consumed by the Cannizzaro reaction which proceeded as a side-reaction. According to ion-chromatographic quantification of the amount of sodium salt of isovaleric acid, 7.71 g (62.1 mmole) of this compound are actually found in the aqueous phase. The aqueous phase furthermore contains 10 wt. % acetone which can be removed by simple rotation in a rotary film evaporator.

In the upper, product-containing, phase the yield and the concentration of by-products are determined by means of quantitative GC with n-dodecane as the internal standard. In the organic phase 26.4 g methyl isobutyl ketone are detected, the result of acetone dimerization under hydrogenating conditions, not taking into account the 35 g methyl isobutyl ketone which was already present at the beginning of the reaction.

Quantification shows that 606.3 g 6-methylheptanone (4.73 mole) were obtained, which corresponds to a 95.4% yield of methylheptanone in relation to isovaleral. The isovaleraldehyde conversion is 99.2%.

The methylheptanone selectivity in relation to acetone is 79.5%, the methylheptanone selectivity in relation to isovaleraldehyde is 96.1%.

No 3-methylbutan-1-ol is detectable in either the organic or the aqueous phase.

EXAMPLES 2–6

The procedure of Example 1 is followed, but using the auxiliary solvents indicated in Table 1. It is clear from the results shown in Table 1 that the addition of lipophilic, difficulty water-soluble auxiliary solvents improves markedly the methylheptanone yield over that of the process without the addition of solvents.

TABLE 1

| Example | Auxiliary Solvent | Conversion (%) | Selectivity (%) | Acetone Selectivity (%) |
|---|---|---|---|---|
| A | — | 99.5 | 93.75 | 78.1 |
| 1 | MIBK[1] | 99.2 | 95.4 | 79.5 |
| 2 | 6-MH[2] | 99.4 | 96.1 | 78.4 |
| 3 | n-hexane | 99.2 | 96.5 | 75.4 |
| 4 | MTBE[3] | 99.2 | 95.9 | 77.5 |
| 5 | cyclohexane | 99.4 | 95.7 | 78.4 |
| 6 | Toluene | 99.8 | 96.5 | 79.4 |

[1]= methyl isobutyl ketone
[2]= 6-methylheptanone
[3]= methyl-tert.-butylether

Comparative Example B
Two-phase Aldolization of Isovaleraldehyde and Acetone With NaOH without Auxiliary Solvent/recycling of the Hydrogenation Catalyst 87.5 kg water are introduced as an initial charge into a 500-liter pressure reactor with a mechanical stirrer, and 1.25 kg NaOH (31.25 mole; 2.5 mol. % in relation to isovaleraldehyde) are dissolved in the water. 1.63 kg hydrogenation catalyst (Pd on carbon, 10 wt. %, product K 0226 from Heraeus, $H_2O$ content 50.0%) are suspended in this solution. After inertization by $N_2$, 108.9 kg (1875 mole) acetone are added to the suspension. A hydrogen pressure of 4 bar is adjusted at room temperature, with intensive stirring. The two-phase mixture is heated to 105° C. 109.2 kg isovaleraldehyde (1255 mole; from Celanese; 99% by GC analysis) are dispensed by diaphragm pump from an initial charge into this mixture by way of a submerged tube. The molar ratio of aldehyde to acetone is thus 1:1.5.

The dispensing period is 3 h, the reaction temperature is maintained at between 105° C. and 110° C., with restraint of the heat which is generated. After dispensing is completed, stirring is continued for one further hour under hydrogen pressure, such that a constant pressure of 8 bar is present throughout the dispensing and post-reaction period. A total of approx. 35 m³ hydrogen is taken up by the batch.

After cooling to room temperature, the two-phase suspension is forced through a pressure filter. The weighed quantity of recycled Pd/C catalyst is 1.85 kg.

After phase separation has been completed 134.2 kg aqueous phase and 183.1 kg organic phase having a 6-methylheptanone content of 81.9% are obtained.

This corresponds to a weighed quantity of 150.0 kg (1170.3 mole) 6-methylheptanone. The reaction selectivity is 93.2% at complete conversion of isovaleraldehyde.

The recyclability of the aldolization catalyst is checked by following the procedure of Comparison Example B and recycling the Pd/C catalyst which is in each case separated following the pressure filtration. The results are shown in Table 2.

TABLE 2

Recyclability of the adolisation catalyst from Comparative Example B

| Recycle count | Conversion (%) | Selectivity (%) | Acetone selectivity, (%) | MIBK[1] kg | HS[2] kg |
|---|---|---|---|---|---|
| 1 | 99.5 | 93.6 | 79.8 | 8.0 | 8.4 |
| 2 | 99.4 | 94.6 | 84.1 | 9.4 | 6.9 |
| 3 | 99.4 | 94.5 | 76.2 | 11.1 | 10.5 |
| 4 | 99.5 | 95.5 | 80.6 | 8.6 | 8.2 |

[1]= methyl isobutyl ketone
[2]= high-boiling compounds; high-boiling by-products

EXAMPLE 7

The procedure of Comparison Example B is followed, with the recycled catalyst which has already been utilized for five batches being used, but replenished with the acetone additionally also 9.2 kg methyl isobutyl ketone (10.5 wt. % in relation to $H_2O$) as well as 4.4 kg 6-methylheptanone (5.0 wt. % in relation to $H_2O$) as auxiliary solvents. The results set out in Table 3 are obtained by the addition of an auxiliary solvent mixture of methylheptanone and methyl isobutyl ketone:

TABLE 3

Recyclability of the aldolization catalyst of Example 7

| Recycle count | Conversion (%) | Selectivity (%) | Acetone selectivity (%) | MIBK kg |
|---|---|---|---|---|
| 5 | 99.4 | 98.2 | 82.5 | 8.9 |

The recycle count relates to the number of cycles of the hydrogenation catalyst without replenishment with fresh material. It becomes clear that a yield increase of approx. 3% is achieved by the addition of the solvent mixture described. No 3-methylbutan-1-ol is detectable in the organic phase.

EXAMPLE 8
Two-phase Aldolization of Citral and Acetone With KOH in the Presence of Methyl Isobutyl Ketone as the Auxiliary Solvent 100 g of an aqueous glycerol solution and 10 g methyl isobutyl ketone are introduced as an initial charge into a 0.5-liter autoclave with a mechanical stirrer, and 1.3 g hydrogenation catalyst (Pd on carbon, 5 wt. %, E 101 R/W Degussa AG, $H_2O$ content 53.9%) are suspended in the batch. 2.24 g KOH (0.04 mole; 4 mol. % in relation to citral) are added to this suspension. When KOH has passed into solution 87.12 g (1.5 mole) acetone are added to this suspension. A hydrogen pressure of 30 bar is adjusted at room temperature, with intensive stirring. The two-phase mixture is heated to 120° C. 153.8 g citral (1.0 mole; from Merck; 99% by GC analysis) are dispensed by HPLC pump from an initial charge into this mixture by way of a submerged tube. The molar ratio of aldehyde to acetone is thus 1:1.5.

The dispensing period is 3 h, the reaction temperature is maintained at between 120° C. and 125° C., with restraint of the heat which is generated. After the addition is completed, stirring is continued for a further two hours under hydrogen pressure, such that a constant pressure of 30 bar is present throughout the dispensing and post-reaction period.

After cooling to room temperature, the autoclave is opened and the catalyst is separated by means of filtration. A slightly yellowish organic phase is obtained which is washed twice in succession, each time with 30 ml water.

In the upper, product-containing, phase the yield and concentration of by-products is (sic) determined by means of quantitative GC with n-dodecane as the internal standard. The citral conversion is 96%, the yield of 6,10-dimethylundecan-2-one along with unsaturated derivatives is 89.2%, which corresponds to a selectivity of 92.2% for the formation of methyl ketones.

EXAMPLE 9
Preparation of Methylheptanone Starting from Prenal (=3-methyl-2-buten-1-al=Dimethyl Acrolein) and Acetone Via Two-phase Catalysis in the Presence of Aqueous Sodium Hydroxide Solution and Methyl Isobutyl Ketone as the Auxiliary Solvent 20 g water together with 3 g methyl isobutyl ketone are introduced as an initial charge into a 300-ml autoclave with a mechanical stirrer, and 0.2 g hydrogenation catalyst (Pd on carbon, 5 wt. %, E 101 R/W Degussa AG, $H_2O$ content 53.9%) is suspended in the batch. 0.2 g NaOH (5 mmole; 1.95 mol. % in relation to dimethyl acrolein) is added to this suspension. When NaOH has passed into solution 22.5 g (0.39 mole) acetone are added to this suspension. A hydrogen pressure of 9 bar is adjusted at room temperature, with intensive stirring. The two-phase mixture is heated to 120° C. 21.5 g dimethyl acrolein (0.255 mole; from Aldrich) from an initial charge are dispensed using an HPLC pump into this mixture by way of a submerged tube. The molar ratio of aldehyde to acetone is thus ~1:1.5.

The dispensing period is 3 h, the reaction time is maintained at between 120° C. and 125° C., with restraint of the heat which is generated. After the addition is completed, stirring is continued for one further hour under hydrogen pressure, such that a constant pressure of 9 to 10 bar is present throughout the dispensing and post-reaction period.

After cooling to room temperature, the autoclave is opened and the two-phase mixture is separated. The catalyst is separated by means of filtration. The aqueous phase is extracted with 2×50 ml diethyl ether, the organic phases are dried with $Na_2SO_4$. In the upper, product-containing, phase the yield, conversion and product selectivity in relation to Prenal is (sic) determined by quantitative GC with n-dodecane as the internal standard.

Quantification shows that 30.1 g 6-methylheptan-2-one (0.235 mole) are obtained in the organic phase, which corresponds to a yield of methylheptanone in relation to Prenal of 92.0%. The Prenal conversion is 97.7%, the product selectivity thus 94.2%.

Comparative Example C

Kuraray Process According to U.S. Pat. No. 5,955, 636

Two-phase Aldolization of Isovaleraldehyde and Acetone With NaOH (Without Auxiliary Solvent) With Simultaneous Dispensing of Both the Aqueous Sodium Hydroxide Solution and the Aldehyde 436 g acetone (=7.5 mole) are introduced as an initial charge into a 2-liter autoclave with a mechanical stirrer, and 6.5 g hydrogenation catalyst (Pd on carbon, 5 wt. %, E 101 R/W Degussa AG, $H_2O$ content 53.9%) are suspended in the acetone. A hydrogen pressure of 15 bar is adjusted at room temperature, with intensive stirring. The two-phase mixture is heated to 105° C. within 30 min. 431 g isovaleraldehyde (4.96 mole; from Celanese; 99% by GC analysis) are dispensed by HPLC pump from an initial charge into this mixture by way of a submerged tube. Using a second HPLC pump, 397 g of a 2 wt. % KOH solution in water are dispensed-in within 3 h. This corresponds to a KOH quantity of 16 g (199 mmole; 4 mol. % in relation to isovaleral).

The molar ratio of aldehyde to acetone is 1:1.5. 5 g NaOH (0.125 mole; 2.5 mol. % in relation to isovaleraldehyde) are added to this suspension.

The dispensing period is 3 h, the reaction temperature is maintained at between 105° C. and 110° C., with restraint of the heat which is generated. After the addition is completed, stirring is continued for one further hour under hydrogen pressure, such that a constant pressure of 20 bar is present throughout the dispensing and post-reaction period. A total of approx. 104 l hydrogen is taken up by the batch.

After cooling to room temperature, the autoclave is opened and the two-phase mixture is extracted by suction by means of $H_2O$ as the purging medium. The catalyst is separated by means of filtration.

After normal working-up the yield and the concentration of by-products is (sic) determined in the upper, product-containing, phase by means of quantitative GC with n-dodecane as the internal standard.

Quantification shows that 585.5 g 6-methylheptanone (4.56 mole) are obtained, which, at a 98.3% isovaleral conversion, corresponds to a yield of 92.9%. The selectivity of the conversion is 94.5% in relation to isovaleral. After quantification of the unreacted acetone in the aqueous and the organic phase, an MH selectivity in relation to acetone of 82.0% results.

11.9 g 3-methylbutan-1-ol (0.13 mole) which have arisen from the hydrogenation of the isovaleral are furthermore found in the organic phase. Thus 2.7% of the isovaleral utilized have been consumed in this side-reaction.

What is claimed is:

1. A Process for the preparation of methyl ketones corresponding to the general formula (1)

(1)

wherein x represents a number between 1 and 3 by the reaction of hydrogen, acetone and an aldehyde corresponding to the general formula (2)

(2)

wherein
x represents a number between 0 and 2 and the broken lines represent in each case olefinic double bonds, comprising reacting the hydrogen, acetone and aldehyde having the general formula 2 in the presence of a catalyst suspension, a polar phase, which contains a suspended heterogeneous hydrogenation catalyst and a dissolved aldolization catalyst containing alkali metal or alkaline earth metal, and an organic solvent which separates itself from the polar catalyst phase to form an organic phase which organic phase substantially comprises non-polar auxiliary solvent and acetone.

2. The process according to claim 1, wherein the reacting step includes forming an initial two phase charge mixture of the polar catalyst phase, with acetone and the hydrophobic auxiliary solvent in the presence of hydrogen, and dispensing the aldehyde having the general formula 2 in continuous manner into the initial charge mixture.

3. The process according to claim 1, wherein the auxiliary solventsare selected from methyl isobutyl ketone or the desired methyl ketone or mixtures of these components.

4. The process according to claim 1, wherein the aldolization catalyst is dissolved in a polyhydric alcohol which also constitutes the suspension medium of the heterogeneous hydrogenation catalyst.

5. The process according to claim 4, wherein the polyhydric alcohol is selected from ethylene glycol, propanediol, butanediol, glycerol, erythritol and isomeric tetritols, pentaerythritol, various pentitols such as arabitol and xylitol, hexitols, polyhydric alcohols that are not derived from sugar alcohols, or isomers and homologues, thereof.

6. The process according to claim 4, wherein the polyhydric alcohol is glycerol.

7. The process according to claim 1, wherein the amounts of hydrogenation catalyst and the aldolization catalyst are at a concentration of from $10^{-2}$ to 50 wt. % in relation to the polyhydric alcohol.

8. The process according to claim 1, wherein the aldolization catalyst is a lithium, sodium, potassium, magnesium, calcium or barium hydroxide or carbonate.

9. The process according to claim 7, wherein the aldolization catalyst is sodium hydroxide.

10. The process according to claim 1, wherein the aldolization catalyst is a basic salt of an alkali metal or alkaline earth metal.

11. The process according to claim 1, wherein the amount of aldolization catalyst is between 0.1 and 10 mol. % in relation to aldehyde utilized.

12. The process according to claim 1, wherein contact catalysts containing palladium or platinum are used as the hydrogenation catalyst, optionally on an inert support.

13. The process according to claim 1, wherein the auxiliary solvents are selected from pentane, hexane, cyclohexane, heptane, octane, benzene, toluene, xylene, diethylether, dibutylether, methyl isobutyl ether, methyl-tert-butylether, tetrahydrofuran, dioxane, glymes, diglymes or 6-methylheptanone.

14. The process according to claim 13, wherein the auxiliary solvent is methyl isobutyl ether.

15. The process according to claim 1, wherein the aldehyde having formual 2 is Prenal or isovaleraldehyde and the methyl ketone having formula 1 is 6-methylhepten-2-one.

16. The process according to claim 1, wherein after termination of the reaction the product phase is separated from the alcohol phase which contains the aldolization catalyst and the suspended hydrogenation catalyst and, after appropriate working-up and replenishment of consumed proportions of catalyst, is utilized again as the catalyst phase.

17. The process according to claim 1, wherein the process is operated in continuous manner, by bringing the organic and polar phases into contact in a co-current or counter-current manner, separating phases and circulating the catalyst phase.

* * * * *